Figure 1:
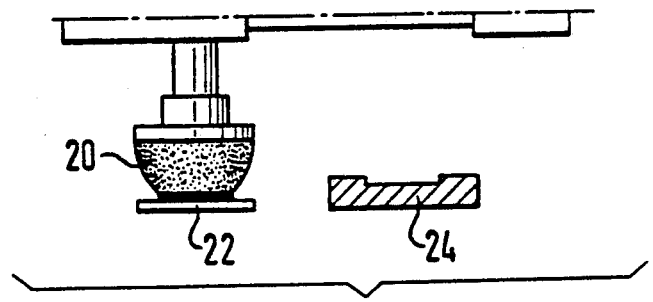

United States Patent [19]
Anhäuser et al.

[11] Patent Number: 5,110,599
[45] Date of Patent: May 5, 1992

[54] PROCESS FOR PRODUCING AN ADMINISTRATION AND/OR DOSAGE FORM FOR MEDICINAL ACTIVE SUBSTANCES BY MEANS OF A PRINTING PROCESS

[75] Inventors: Dieter Anhäuser, Melsbach; Robert-Peter Klein, Neuwied, both of Fed. Rep. of Germany

[73] Assignee: LTS Lohmann Therapie-Systeme GmbH & Co. KG, Neuwied, Fed. Rep. of Germany

[21] Appl. No.: 746,296

[22] Filed: Aug. 13, 1991

Related U.S. Application Data

[63] Continuation of Ser. No. 544,011, Jun. 26, 1990, abandoned, which is a continuation of Ser. No. 348,588, filed as PCT/DE88/00366, Jun. 16, 1988, abandoned.

[30] Foreign Application Priority Data

Aug. 14, 1987 [DE] Fed. Rep. of Germany ....... 3727232

[51] Int. Cl.⁵ ............................................. A61F 13/00
[52] U.S. Cl. .......................................... 424/449; 427/3
[58] Field of Search .................... 427/3; 424/443, 449, 424/467

[56] References Cited

U.S. PATENT DOCUMENTS

| | | | |
|---|---|---|---|
| 2,865,810 | 12/1958 | Sanders, Jr. | 424/467 |
| 3,015,609 | 1/1962 | Sanders, Jr. | 424/467 |
| 3,910,183 | 10/1975 | Noren et al. | 264/132 X |
| 4,409,264 | 10/1983 | Gilleo et al. | 427/265 |
| 4,548,825 | 10/1985 | Voss et al. | 427/3 X |
| 4,699,792 | 10/1987 | Nick et al. | 424/446 |
| 4,711,781 | 12/1987 | Nick et al. | 426/448 |
| 4,743,249 | 5/1988 | Loveland | 424/447 |

Primary Examiner—Thurman K. Page
Assistant Examiner—Leon R. Horne
Attorney, Agent, or Firm—Kalish & Gilster

[57] ABSTRACT

The invention relates to a process for producing an administration and/or dosage form for medicament active substances using a printing process, in which the printing process used is a pad printing process.

9 Claims, 2 Drawing Sheets

PROCESS FOR PRODUCING AN ADMINISTRATION AND/OR DOSAGE FORM FOR MEDICINAL ACTIVE SUBSTANCES BY MEANS OF A PRINTING PROCESS

This application is a continuation of application Ser. No. 07/544,011, filed Jun. 26, 1990, now abandoned, which is a continuation of Ser. No. 348,588, filed as PCT/DE88/00366, June 16, 1988, now abandoned.

DESCRIPTION

The invention relates to a process for producing an administration and/or dosage form for medicinal active substances by means of a printing process.

This application is a continuation of Ser. No. 544,011 filed Jun. 26, 1990, abandoned which is a continuation of 348,585, filed Mar. 23, 1989, abandoned.

The use of printing processes for producing medicaments has been described in EP-OS 219 762, where a two-dimensional administration form of a medicament, comprising a water-soluble carrier film and an active substance containing coating is produced, in that the coating material is continuously applied by means of a roller application process used in printing technology to at least one side of the carrier film. The weight constancy attainable with this process in the case of a web speed of several 100 m/min approximately $\pm 10\%$. Application of the coating material takes place with rollers having a special fine engraving, the engraved in grooves forming an angle of preferably 45° to the carrier film movement direction. This process permits the transfer of coatings up to 80 g/m², but only planar surfaces can be printed.

These roller application processes are disadvantages in that they are only suitable for large surfaces, but leave much to be desired as regards their application accuracy. Moreover, e.g. in the production of circular medicament shapes, they lead to a large amount of waste.

These processes requiring large equipment are not suitable for readily evaporating materials, expensive active substances or small production quantities. They are also difficult to incorporate into existing production processes. It is also disadvantageous that they are only able to uniformly print planar surfaces, whereas uneven surfaces cannot be printed.

For the production of medicament administration forms with highly active and optionally volatile active substances and high demands as regards constant dosage quantities, as well as optionally uneven substrates to which the substance should be applied, it has hitherto been conventional practice to use e.g. dosing pumps, e.g. piston dosing pumps for the active substances, which deliver precisely dosed quantities. Such dosing pumps are expensive to purchase and complicated to maintain, particularly if they are designed for dosing very small quantities.

The problem of the present invention is therefore to provide a new process for the precise material application in connection with the production of medicament administration and/or dosage forms.

According to the invention this problem is solved by the process being a pad printing process.

Pad printing processes have been known since 1968 and are also suitable for printing uneven surfaces to which adapt the flexible, printing medium-transferring pads. A pad printer is e.g. described in DE-OS 19 39 437. The pictorial element to be printed is etched in sunk form into a block, i.e. the printing form. The printing medium is transferred into this block and following a doctor blade process which doses the printing medium received in the block, the pad completely absorbs the printing medium left behind in the block and transfers it to the object to be printed. A survey concerning uses and characteristics of the pad printing process appears in the brochure of TAMPOPRINT GmbH, Daimlerstrasse 27/1, Korntal-Munchingen, to which reference is made in order to avoid unnecessary repetition.

Due to their limited space requirements pad printers are particularly suitable for the inventive use, because they can be integrated without difficulty into production lines and can also be encapsulated, which is helpful when processing highly active medicaments for the purpose of protecting operating personnel, as well as for avoiding the evaporation of volatile substances. In encapsulated systems, it is also possible to operate under inert gas, such as nitrogen, argon, etc., which can be appropriate in the case of oxygen-sensitive substances.

No attempt has been made hitherto to use pad printers for delivering precisely controlled quantities of printing medium with a weight per unit area of over approximately 30 g/m². It has suprisingly been found that the pad printing process permits a precise dosing of weights per unit area of up to 200 g/m² in a printing process with a variance of $\pm 2\%$ and under.

As stated in the parallel German patent application filed on the same date by the present Applicant and entitled "Pad printer with increased printing medium delivery", it is possible by varying the pad material (more printing medium being transferred in the case of softer pads) and the pad surface (enlargement by introducing depressions, such as grooves, cups, etc.), as well as the viscosity of the printing medium to unexpectedly increase the printing medium quantity delivered in a printing process and despite this to obtain a dosing remaining constant within narrow limits.

As a result of the inventive process, it is now possible for the first time to produce small active substance doses without active substance loss, such as was the case in the hitherto used surface coating process, e.g. for transdermal, therapeutic systems, in any desired design, such as a circle, triangle, oval, etc., whereby during the application of the active substances expensive active substance is saved and it is possible without difficulty to obviate the problem of active substance waste elimination.

In a preferred embodiment of the inventive process the administration and dosage form is a dermally applicable system. The term "dermal absorption" is here understood to mean any absorption by the skin or enclosed mucous membranes and this consequently also covers rectal and vaginal administration forms, such as suppositories or the like.

Particularly preferred dermally applicable systems are transdermal, therapeutic systems, e.g. an active substance-containing plaster, such as are e.g. described in German patent 36 29 304.

The inventive process can also be used if the administration form is an orally administrable system, such as a tablet, capsule, etc.

The inventive process permits the production of many components of administration forms, such as adhesive coatings and spots, inscriptions on tablets, active substance-containing areas, etc.

It is also possible in one production stage and by using suitable blocks to simultaneously apply several printing media, such as e.g. an adhesive area and an aseptic or active substance-containing area in the case of plasters or therapeutic systems. Both the block and the pad can be thermally controlled, if it is necessary to process temperature-sensitive materials or those only processable in the heated state, such as certain adhesives.

In one printing process it is possible to transfer a weight per unit area of up to approximately 200 g/m² of printing medium. A further improvement to the transfer quantity can be achieved by improvements to the process which are obvious to the Expert and such as are more particularly described in the Applicant's parallel application entitled "Pad printing device for transferring clearly defined quantities of printing medium per surface unit".

A particular advantage of the inventive process is the decisively improved medicament safety and reliability, because highly active medicaments can be dosed much more accurately than hitherto. The application of excess material is prevented.

Further features and advantages of the invention can be gathered from the following description relative to the drawings, wherein show:

FIG. 1 A pad printer on applying an active substance coating to a plaster-like therapeutic system.

Figure 2:
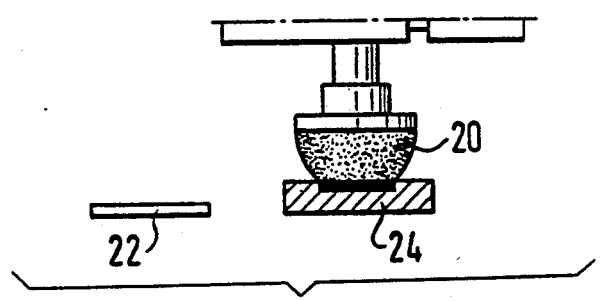

FIG. 2 The pad printer of FIG. 1 on taking up new active substance from the block.

Figure 3:
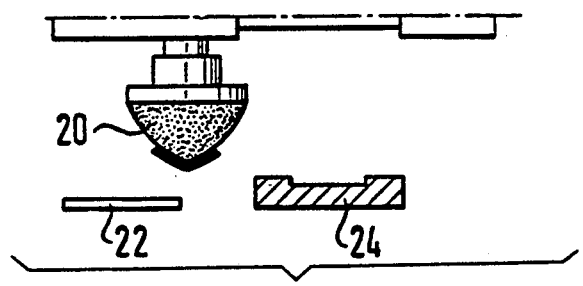

FIG. 3 The printing medium-coated pad in the transfer from the block to the substrate.

Figure 4:
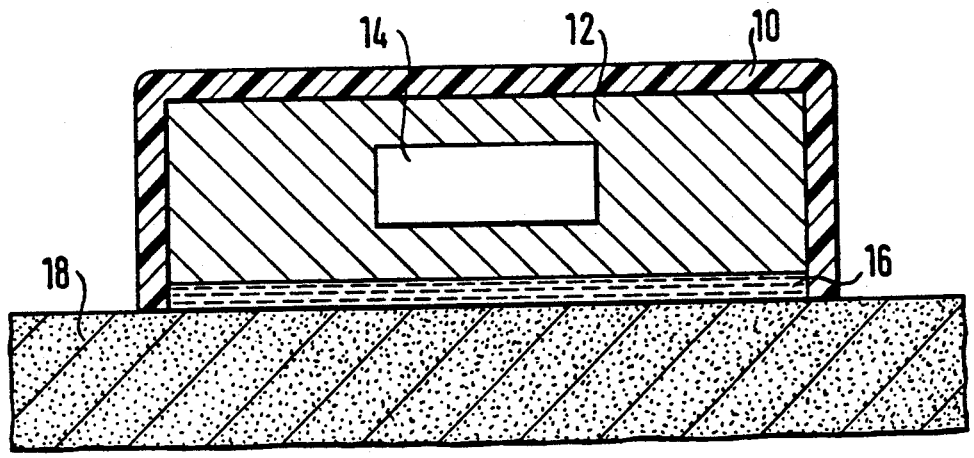

FIG. 4 A cross-section through a transdermal, plaster-like therapeutic system produced according to the inventive process.

Figure 5:
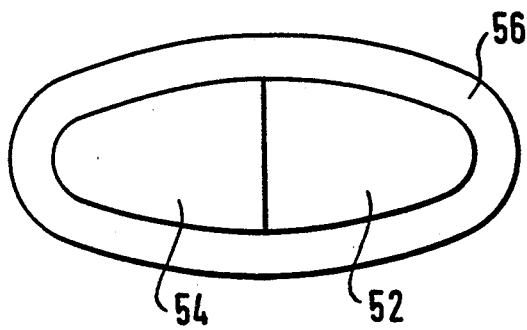

FIG. 5 A plan view of a further transdermal, therapeutic system produced by the pad printing process with the adhesive coating removed and with two different active substances.

Figure 6:
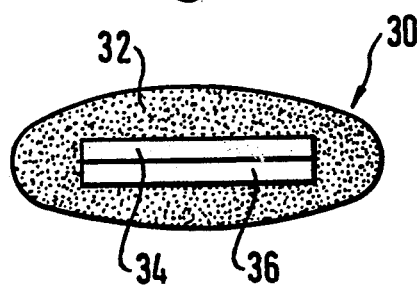

FIG. 6 A further preferred administration form produced by the inventive process constituted by a tablet.

As shown in FIG. 1, an elastic, oval silicone rubber pad 20 with an active substance-containing printing medium coating is printed on a flat substrate, here on a polyethylene film 22 suitable for a plaster backing, so as to leave the coating on substance 22 following the raising thereof.

FIG. 2 shows how the active substance-containing printing medium is absorbed. The pad 20 is pressed onto a block 24, a plate provided with a cavity, in which the printing medium is introduced and is preferably smoothed and dosed by a not shown doctor blade, so as to absorb the printing medium in the cavity. As shown in FIG. 3, the pad 20 is printing medium-coated form is then swung onto the substrate 22 in order to print the same. The supply of the printing medium can take place in a timed or cyclic manner, the time subsequent supply taking place through a storage container terminated by the block 24 and which contains the printing medium. Whilst the pad 20 is pressing on substrate 22, the storage container is moved in timed manner over the cavity in the block and leaves behind there a uniformly distributed printing medium quantity which is defined by the etching depth and which after swinging away the block and simultaneous stripping of the excess printing medium in the next cycle is raised from the pad 20 and transferred to the next substrate 22 to be printed. The printed substrate coating can now be covered by a cover coating in the next station of the production line, so that the printing medium is not subject to prolonged exposure to the atmosphere, which could damage the substance in the case of light-sensitive substances or cause evaporation in the case of printing media with a high vapour pressure, etc.

FIG. 4 shows a plaster-like, transdermal, therapeutic system partly produced according to the inventive process. The system is covered by an active substance-impermeable cover film 10, below which is located an active substance distribution matrix 12, which in this case is contact adhesive and which can be applied in a number of stages by the inventive printing process. An active substance reservoir 14 with a different composition is embedded in the contact adhesive coating. This is finally followed by a control coating 16 with a predetermined thickness and which can be applied by the inventive process, in order to control the active substances diffusing out of the active substance distribution matrix.

FIG. 5 illustrates a further application possibility with the inventive process for transdermal systems, in which case the system backing has been removed and the two active substance reservoirs 52, 54 are fully visible.

In this case two semioval, active substance-containing coatings 52, 54 are printed on an adhesive material coating 56, which can be subsequently coated by an adhesive backing (which is in this case removed and not shown). This reveals the superior operation of the inventive process in the production of multicomponent systems with a high coating accuracy. FIG. 6 shows a tablet 30 with a sugar covering 32, which has a two-coating depot. The sugar covering encloses a two-coat active substance product, with coats 36, 34, whereof coat 36 is produced by printing on 34 using the pad printing process.

A preferred variant of the inventive process is described hereinafter in conjunction with the production of nicotine plasters.

EXAMPLES

Production of a Nicotine Plaster

A pad printer with a steel block having a circular cavity of 39 mm and an etching depth of 240 micrometers as the printing style is used for printing substrates. The pad is constituted by an oval silicone foam rubber pad with a Shore hardness of 6.

The printing medium used was a 50% by weight solution of nicotine in Miglyol 812, an oil produced and marketed by Dynamit Nobel with a viscosity of 44 dPa/s at 21° C. The pad applies circular coatings of this printing medium to a contact adhesive-coated substrate. The substrate is constituted by an aluminum vapour coated 100 micrometer thick, siliconized polyester film, i.e. the protective coating to be subsequently removed prior to using the plaster, having an acrylate contact adhesive coating (30 g/m²), printing then taking place on the acrylate surface. Solution quantities of 91 mg are applied to a 12 cm² surface in the case of a limit of error below 5%.

The printed substrate was then lined and prepared in per se known manner with a 16 micrometer thick, aluminium vapour coated polyester film with an acrylate priming coat forming the plaster backing.

The structure of the finished nicotine plaster roughly corresponds to that of the plaster shown in FIG. 4.

We claim:

1. Process for producing a medicament active substance dosage on a substrate, comprising the steps, in sequence, of (a) applying a quantity of the active substance as a printing medium to a cavity of a printing pad block, (b) pressing a deformable printing pad onto the block cavity to absorb the active substance printing medium, and (c) pressing the pad with the absorbed active substance printing medium to a substrate to leave on the substrate a precisely controlled printed dosage coating of the medicament active substance wherein the printing medium is for administration in a transdermal therapeutic system has been inserted.

2. Process according to claim 1 wherein the pad is silicone foam rubber.

3. Process according to claim 2 wherein the substrate is polyester film.

4. Process according to claim 1 wherein the printing medium is for administration in a dermally appliable system.

5. Process according to claim 1 wherein the printing medium comprises an oil solution of nicotine for use in a nicotine plaster.

6. Process according to claim 1 further comprising, after step (c), the step of (d) covering the printed dosage coating with a cover coating.

7. Process according to claim 1, wherein the step (c) further comprises pressing the pad with the absorbed active substance printing medium to a substrate which is flat.

8. Process according to claim 1, wherein the step (c) further comprises pressing the pad with the absorbed active substance printing medium to a substrate which is uneven.

9. Process according to claim 1, wherein the steps (a), (b) and (c) are repeated in a timed, continuous cycle so as to leave on the substrate a quantity of uniformly distributed printing medium.

* * * * *

UNITED STATES PATENT AND TRADEMARK OFFICE
CERTIFICATE OF CORRECTION

PATENT NO. : 5,110,599

DATED : May 5, 1992

INVENTOR(S) : Dieter Anhauser, et al.

It is certified that error appears in the above-identified patent and that said Letters Patent is hereby corrected as shown below:

Column 5, line 12, delete "has been inserted".

Signed and Sealed this

Fourth Day of October, 1994

Attest:

BRUCE LEHMAN

*Attesting Officer*    *Commissioner of Patents and Trademarks*